United States Patent [19]
Tabata et al.

[11] Patent Number: 6,077,794
[45] Date of Patent: Jun. 20, 2000

[54] DEODORANT FIBROUS MATERIAL AND METHOD OF PRODUCING THE SAME

[75] Inventors: Jirou Tabata; Toshiharu Kanaya; Masayuki Hirata; Kouichi Saito, all of Shiga; Kouji Hori; Kouichi Kawaguchi, both of Wakayama, all of Japan

[73] Assignee: Toray Industries, Inc., Japan

[21] Appl. No.: 08/871,527

[22] Filed: Jun. 9, 1997

[30] Foreign Application Priority Data

| Jun. 11, 1996 | [JP] | Japan | 8-149166 |
| Aug. 22, 1996 | [JP] | Japan | 8-221196 |
| Feb. 14, 1997 | [JP] | Japan | 9-30106 |
| Feb. 17, 1997 | [JP] | Japan | 9-32239 |

[51] Int. Cl.$^7$ ........................... B32B 27/02
[52] U.S. Cl. .................. 442/123; 442/417; 428/365; 428/368; 428/375; 427/180; 427/372.2
[58] Field of Search .................... 442/123, 417; 428/365, 368, 375; 427/180, 372.2

[56] References Cited

FOREIGN PATENT DOCUMENTS

| 116865 | 8/1984 | European Pat. Off. . |
| 3076867 | 4/1991 | Japan . |
| 08280781 | 10/1996 | Japan . |

*Primary Examiner*—Elizabeth M. Cole
*Attorney, Agent, or Firm*—Austin R. Miller

[57] ABSTRACT

A deodorant fibrous material contains (1), as a first deodorant material, at least one deodorant component selected from inorganic type and polyorganic acid, ester or salt type components, (2), as a second deodorant material, at least one of a hydrazine compound and a specified polyvinyl amine compound and (3) a synthetic resin binder. The deodorant fibrous material can be produced by applying to a fibrous material, by a padding or coating method, a liquid composition containing the above components (1)–(3), followed by subsequent heat treatment.

17 Claims, No Drawings

DEODORANT FIBROUS MATERIAL AND METHOD OF PRODUCING THE SAME

TECHNICAL FIELD

The present invention relates to a deodorant fibrous material and a method of producing the material and, more particularly, to a deodorant fibrous material that has a durable excellent deodorizing characteristic for bad odors, such as ammonium, amines, hydrogen sulfide, mercaptans and the like, and aldehydes, acetic acid and the like contained in tobacco odors, and the like, and that has a soft texture, and a method of producing the deodorant fibrous material.

BACKGROUND ART

Recently there has been a further growing demand for high level deodorizing functions provided in fibrous products such as clothing, household articles, interior products, various industrial materials and the like. Conventionally proposed as methods for providing deodorizing characteristics for fibrous materials are a method in which a deodorant substance is kneaded into the interior of polymers during synthetic fiber yarn production and a method in which a deodorizing agent is fixed to surfaces of fibers with a binder. As an example of the former method, a polyester fiber (Japanese patent publication (Kokoku) No. Hei JP-B-7-81206) containing titanium dioxide particles carrying phthalocyanine polycarboxylate thereon or the like may be cited. As an example of the latter method, a fiber (Japanese patent application laid-open (Kokai) No. Hei JP- A-7-189120) coated with a deodorization catalyst for oxidative decomposition of odor components, or the like, may be cited.

However, according to conventional methods, the kinds of odor component that can be deodorized are limited, and the deodorization effect on, for example, complex odors such as tobacco odor, containing large amounts of odor component such as aldehydes, acetic acid and the like, is insufficient Furthermore, the conventional methods have problems in that for selection of deodorizing agents, the particle diameter, heat resistance, the affinity to fibrous polymer and the like are remarkably restricted, and the physical properties of material yarn are degraded. In addition, the aforementioned latter method has problems in that the texture becomes rough, and the washing durability is low, etc.

DISCLOSURE OF THE INVENTION

It is an object of the present invention to provide a deodorant fibrous material that has a durable excellent deodorizing characteristic for bad odors, such as ammonium, amines, hydrogen sulfide, mercaptans and the like, and aldehydes, acetic acid and the like contained in tobacco odors, and the like, and that can be provided with a soft texture, and a method of producing the deodorant fibrous material.

One aspect of the present invention provides a fibrous material wherein (1) an inorganic type component partially or entirely replaceable by a polyorganic acid, ester or salt thereof), (2) a polyvinyl amine compound indicated by the following general formula [I] and/or a hydrazide compound and (3) a synthetic resin are attached to a surface of a fibrous material.

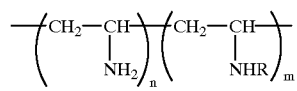

(In the formula, R indicates a CHO group or a CH 3 CO group, and n and m, independently of one another, are respective integers.)

Another aspect of the present invention provides a product formed from the aforementioned deodorant fibrous material. Yet another aspect of the invention provides a method of producing a deodorant fibrous material comprising applying to a surface of a fibrous material, preferably by a padding or coating method, a liquid deodorant composition comprising each of the abovementioned components (1)–(3), each of which respective components may be, independently of one another, dispersed or dissolved in a liquid medium, and then subjecting the fibrous material to heat treatment.

Prior to application of the deodorant composition as described above, the fibrous material may be subjected to immersion in a treatment bath of a liquid containing a cycloalkane halide compound. Especially after pretreatment with the cycloalkane halide compound, the fibrous material may be treated with a deodorant composition containing, in addition to the deodorant and binder components (1)–(3) a copolymer of a polyalkylene glycol with an aromatic dicarboxylic acid and an alkylene glycol. The present invention is able to produce a durable and excellent deodorizing characteristic for bad odors, such as ammonium, amines, hydrogen sulfide, mercaptans and the like, and aldehydes, acetic acid and the like contained in tobacco odors, and the like, and also provide a soft texture.

BEST MODE FOR CARRYING OUT THE INVENTION

As a fibrous material for use in the present invention, any fiber that is conventionally used for fibrous products, such as clothes, house furnishings, interior products and various industrial materials may be used. For example, synthetic fibers or semi-synthetic fibers formed from a synthetic resin, for example, a polyalkylene terephthalate such as polyethylene terephthalate, polybutylene terephthalate or the like, or a polyester copolymer of a polyalkylene terephthalate mentioned above and a third component, a polyamide such as nylon 6, nylon 66 or the like, a polyamide copolymer of a polyamide mentioned above and a third component, a polyolefin such as polyethylene, polypropylene or the like, polyvinyl chloride, an acrylic resin, an acetate resin, or the like, a regenerated fiber such as Bemberg, rayon or the like, a cellulosic fiber such as cotton, flax, hemp, ramie, jute, Manila hemp or the like, a protein type fiber such as wool, silk or the like, or the like, may be cited.

These fibers may be used separately as a single component or in the form of a composite fibrous material obtained by blending, filament-combining, twisting, or weaving or knitting two or more species of the fibers. The fiber may take various forms, for example, filament, staple, textile, non-woven fabric, sewed products or the like.

These fibrous materials may be materials containing or treated with an additive, such as a dye, a pigment, an anti-oxidizing agent, a heat resistant agent, an anti-UV agent, a plasticizing agent, an antibacterial agent, a flame retardant agent or the like, which has been added in a fiber production step or a post-processing step.

Among the aforementioned fibrous materials, a polyester fiber formed from a polyester, such as polyethylene terephthalate, polybutylene terephthalate or the like, or a textile, a non-woven fabric or a sewed product containing a polyester fiber mentioned above, may be suitably used as a fibrous material for the present invention. The polyester is particularly suitable if used in a material provided with flame retardancy by a cycloalkane halide compound.

As a deodorizing agent in the deodorant fibrous material of the present invention, inorganic type components, i.e. components providing at least one inorganic element (but including active carbon), and polyvinyl amine compounds indicated by the general formula [I] and/or hydrazide compounds may be used.

Preferably used as an inorganic type component are porous substances formed from silicon dioxide, titanium dioxide, zinc oxide, aluminum oxide or the like, porous substances such as zeolite, silica gel, active carbon or the like, or organic acid salts such as acetates or citrates, inorganic acid salts such as sulfates or nitrates, chlorides, hydroxides or oxides of metal such as copper, zinc, silver, lead, iron, aluminum, calcium, magnesium, manganese, nickel, cobalt or the like, and the like. Particularly preferred are copper compounds that chelates with nitrogen atoms in a synthetic resin thereby improving the compatibility of the treating liquid and improving the washing durability of these compounds.

The average particle diameter of the porous substance used as an inorganic type compound is preferably 0.3–100 $\mu$m and, particularly preferably, 0.5–10 $\mu$m, if the porous substance is a compound difficult to dissolve in water. If the average particle diameter is greater than 100 $\mu$m, the surface roughness feel of the fibrous material becomes considerable, and the texture also becomes rough and hard. If the average particle diameter is too small, industrial production becomes difficult, causing a reduction in productivity. Therefore, it is preferably at least 0.3 $\mu$m.

As for a porous substance, amorphous substances formed from silicon dioxide and zinc oxide are particularly preferred among the aforementioned substances. It is preferred that among such porous substances, a porous substance having a specific surface area of 10–150 m$^2$/g and, preferably, 50–100 m$^2$/g be used.

If a metallic compound of at least one of copper and zinc is used as an inorganic type compound, the deodorization effect on odors, such as hydrogen sulfide or mercaptans, can be increased. As preferred examples of the metallic compound of zinc or copper, organic acid salts such as citrates, acetates and the like, inorganic acid salts such as nitrates, sulfates, chlorides, hydroxides, oxides of copper or zinc may be cited.

The amount of the inorganic type compound attached is preferably 0.05–10% owf and, more preferably, 0.1–5% owf relative to the fibrous material. If the amount attached is less than 0.05% owf, it becomes hard to obtain a sufficient deodorization effect. If it is greater than 10% owf, there is a tendency that the texture of the fibrous material will become rough and hard and the surface roughness feel will increase. In the case of a dyed product, the shade or tint dulling tends to increase.

The polyvinyl amine compound indicated by the general formula [I] has an effect as a deodorizing agent in the deodorization of aldehydes. The polyvinyl amine compound can be obtained by polymerization of N-vinyl formmide, N-vinyl acetamide or the like in an aqueous solution followed by hydrolysis by an acid or a base. It is also possible to copolymerize other type of vinyl monomers, for example, acrylic acid, acrylamide, acrylonitrile, ethylene, styrene, vinyl acetate or the like during the polymerization of the polyvinyl amine compound.

The molecular weight of the polyvinyl amine compound is preferably within a range of about 10,000 to about 200,000. If the molecular weight is less than 10,000, the water solubility increases so that the washing durability after attachment to the fibrous material becomes insufficient. If the molecular weight is greater than 200,000, the viscosity increases so that it becomes difficult to mix with the inorganic type compound. In said general formula [I], n is preferably within a range of about 150 to 4650, and m is preferably within a range of about 0 to 850.

As examples of the hydrazide compound used according to the present invention, monohydrazides such as formohydrazide, acetohydrazide, hydrazide propionate, hydrazide laurate, hydrazide stearate, hydrazide salicylate, hydrazide benzoate, hydrazide p-hydroxybenzoate, methyl carbazate, ethyl carbazate, semicarbazide hydrochloride and the like, dihydrazides such as carbohydrazide, dihydrazide oxalate, dihydrazide malonate, dihydrazide succinate, dihydrazide glutarate, dihydrazide adipate, dihydrazide pimelate, dihydrazide suberate, dihydrazide azelate, dihydrazide sebacate, dihydrazide terephthalate, dihydrazide isophthalate, dihydrazide tartarate, dihydrazide malate, dihydrazide iminodiacetate, dihydrazide itaconate, dodecane dihydrazide, hexadecane dihydrazide, dihydrazide 2,6-naphthoate, dihydrazide 1,4-naphthoate, 4,4-bisbenzene dihydrazide, 2,6-pyridine dihydrazide, 1,4-cyclohexanedihydrazide, N,N'-hexamethylene bis-semicarbazide and the like, trihydrazides such as trihydrazide citrate, trihydrazide pyromellitate, 1,2,4-benzene trihydrazide, trihydrazide nitriloacetate, trihydrazide cyclohexane tricarboxylate and the like, tetrahydrazides, such as tetrahydrazide ethylenediamine tetraacetate, tetrahydrazide 1,4,5,8-naphthoate and the like may be cited. Hydrazide compounds having two or more hydrazino groups are particularly suitable.

The amount of polyamine compound or hydrazide compound attached is preferably 0.01–20% owf and, more preferably, 0.05–5% owf relative to the fibrous material. If the amount attached is less than 0.01% owf, there is a tendency that the it will become difficult to obtain a sufficient deodorizing effect on aldehydes. If it is greater than 20% owf, there is a tendency that the texture of the fibrous material will become rough and hard.

According to the present invention, it is extremely preferred to use an emulsifying dispersion agent in order to uniformly disperse an inorganic type compound used as a deodorizing agent in an aqueous solution and, thereby, prevent precipitation of the inorganic type compound. This is because if an inorganic type compound and a polyvinyl amine compound or a hydrazide compound and a synthetic resin are simply mixed, aggregation will occur so that uniform attachment to a surface of the fibrous material cannot be achieved. A preferred emulsifying dispersion agent is a polyvinyl alcohol or a solvent that has penetrating characteristics; i.e. that is capable of penetrating the fibrous material.

Polyvinyl alcohol is effective not only as an emulsifying dispersion agent but also as an agent for improving the washing durability of the inorganic type compound. The molecular weight of the polyvinyl alcohol is preferably about 2000–100,000 and, more preferably, 5000–50,000. If the molecular weight is less than 2000, the viscosity of the deodorizing agent will be small and there is a tendency that the inorganic type compound will not uniformly disperse but precipitate, or a tendency that the texture of the fibrous material will become rough and hard if a crosslinking agent is present. If the molecular weight is greater than 100,000, there is a tendency that the water solubility will become small and the function as an emulsifying dispersion agent will not readily be achieved.

As examples of the solvent having a penetrating characteristic for uniformly dispersing the inorganic type compound while preventing aggregation thereof, alcohols, glycols, cellosolve and the like may be cited. Particularly, isopropyl alcohol, methanol, ethanol, ethylene glycol, propylene glycol, methyl cellosolve, ethyl cellosolve and the like are suitable.

A synthetic resin used according to the present invention is a synthetic resin that is to function as a binder for retaining (attaching) the inorganic type compound and the polyamine compound or hydrazide compound used as deodorizing agents, onto a surface of the fibrous material. As preferable synthetic resins, urethane based resin, acrylic based resin, aminoplast resin, epoxy based resin, glyoxal based resin, ethylene urea resin and the like may be cited. Among these, urethane based resin or acrylic based resin are preferable in view of texture and durability. Particularly preferred is urethane based resin.

The urethane resin is preferably used in the form of a polyurethane resin based emulsion or aqueous solution. As specific examples of the polyurethane resin based emulsion or aqueous solution, "Elastoron" (trade name) and "SuperFlex" (trade name) by Dai-ichi Kogyo Seiyaku (Kabushiki Gaisha), "Hydran" (trade name) by Dainippon Ink Kagaku Kogyo (Kabushiki Gaisha), and the like may be used.

The amount of synthetic resin attached to the fibrous material is preferably 0.01–10% owf and, more preferably, 0.03–2% owf. If the amount of synthetic resin attached is less than 0.01% owf, the washing durability becomes insufficient. If it is greater than 10% owf, there is a tendency that the texture of the fibrous material will become rough and hard.

According to the present invention, it is possible to use a poly-organic acid, ester or salt in place of or together with the aforementioned metallic compound formed from copper, zinc or the like. As examples of the poly-organic acid, ester or poly-organic acid salt, copolymers of appropriate combinations of polyacrylic add, polymethacrylic acid and alkyl esters of these substances, and vinyl acetate, vinyl chloride, vinylidene chloride, allylsulfonic acid, methacrylsulfonic acid, vinyl sulfonic acid, styrene sulfonic acid and the like, and metallic salts of these substances and metals such as copper, zinc, silver, lead, iron, aluminum, calcium, magnesium, manganese, nickel, cobalt and the like, may be cited The poly-organic acid, ester or salt may be present on a porous inorganic type component.

The amount of poly-organic acid, acid ester or acid salt attached to the fibrous material is preferably 0.01–10% owf and, particularly preferably, within the range of 0.03–2% owf. If the amount of poly-organic acid, ester or salt attached is less than 0.01% owf, the deodorizing characteristic becomes insufficient. If it is greater than 10% owf, there is a tendency that the texture of the fibrous material will become rough and hard.

The deodorant fibrous material of the present invention achieves excellent advantages when applied to polyester fibers and is particularly suitable for application to a polyester provided with flame retardancy by a cycloalkane halide compound, as stated above.

The cycloalkane halide compound used as a flame retardant agent is a cyclic saturated carbohydrate compound or a saturated carbohydrate compound having at least one cyclic saturated carbohydrate group, in which at least one hydrogen atom is substituted by a halogen such as bromine, chlorine or the like. As specific examples of the cycloalkane halide, 1,2,3,4,5,6-hexabromocyclohexane, 1,2,3,4-tetrabromocyclooctane (TBCO), 1,2,5,6,9,10-hexabromocyclododecane (HBCD), 1,2-bis-(3,4-dibromocyclohexyl)-1,2-dibromoethane, and those compounds wherein bromine is substituted by chlorine, and the like may be cited Among these, compounds wherein most or all of the halogens are bromine are particularly preferably used since they achieve very high uptake efficiency.

The cycloalkane halide compound is compounded into polyester before fiber forming, or provided on a surface of the polyester fiber after fiber forming. The content is preferably 1.0–20% owf relative to the polyester fiber. If it is less than 1.0% owf, the flame retardancy is low and the flame retardancy is likely to further decrease by the deodorizing processing. If the content exceeds 20% owf, the uptake efficiency decreases and an economic loss increases and, moreover, the anti-light fastness decreases. In a preferred deodorant fibrous material embodying the invention, the deodorant composition attached to the surface of the fibrous material additionally comprises, as a fire retardant, a copolymer of a polyalkylene glycol, an aromatic dicarboxylic acid and an alkylene glycol. The polyalkylene glycol may be a glycol having a main chain of —(C n Hc 2n O)—(n=2–4) and a molecular weight of 300–40,000 and, preferably, 1,000–10,000. For example, polyethylene glycol, polypropylene glycol or block polymers of these compounds, and the like, may be used. If the molecular weight is 300 or less, the durability is insufficient. A molecular weight of 40,000 or greater is not preferable, since the dispersibility decreases with such a molecular weight.

The aromatic dicarboxylic acid is, for example, terephthalic acid or a lower alkyl ester of terephthalic acid and/or isophthalic acid or a lower alkyl ester of isophthalic acid.

The alkylene glycol is, for example, a compound represented by the general formula:

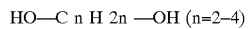

HO—C n H 2n —OH (n=2–4)

For example, ethylene glycol, propylene glycol, butylene glycol and the like may be cited. The block copolymerization mole ratio of a block copolymer of polyalkylene glycol, aromatic dicarboxylic acid and alkylene glycol is preferably 1–31:1:2–3 for improved stainproofness. It is recommended that the block copolymer be dispersed in water with a nonionic or anionic surface active agent, for use.

The block copolymer attached to the fibrous material is preferably present to a solid content of 0.01–3% by weight and, more preferably, 0.05–0.5% by weight relative to the weight of the fibrous material, which is preferably a polyester based fibrous material. By providing the block copolymer, it becomes possible to prevent metal soap combined with Ca ions or Mg ions in the liquid from depositing on the polyester based fiber during washing with water. If the amount of block copolymer provided is 0.01% by weight or less, the stainproofness is not sufficiently achieved and the amount of metal soap remaining after washing increases so that the flame retardancy considerably decreases. If it is 3% by weight or greater, the texture of fabric produced from the fibrous material becomes hard and the dye fastness decreases. Thus, such an amount is not preferable in practical use.

As for the method for applying a cycloalkane halide to the polyester based fiber, immersion in a liquid bath, a padding method and the like may be used. The immersion treatment is particularly preferable having regard to uptake efficiency. As for the immersion treatment conditions, the treatment is preferably performed at 110–150° C. and, more preferably, 120–140° C., normally for 10–60 minutes. The immersion treatment is preferably carried out simultaneously with the normal dyeing process of the polyester based fiber. That is, it is possible to use a cycloalkane compound together with a dyestuff, such as a disperse dye, in a dyebath during the process for dyeing the polyester based fiber.

If a polyester fiber containing a cycloalkane halide compound is used as a fiber material according to the present invention, the amount of the synthetic resin attached to the synthetic resin fiber material is preferably 0.01–2% owf and, particularly preferably, within the range of 0.1–1% owf, in order to achieve a sufficient flame retardancy.

The deodorant fibrous material of the present invention can be produced by treating a fibrous material with a treating liquid containing an inorganic type compound as mentioned above, a polyvinyl amine compound indicated by the general formula [I], or a hydrazide compound, and a synthetic resin, and then heat-treating the material.

The treating liquid may further contain any one or more of a texture processing agent, a finishing agent to impart softness, an antistatic agent, a flame retardant agent, an antibacterial and anti-odor processing agent, a water repellency agent, a stainproof agent and the like, as long as the desired deodorizing characteristic is not particularly impaired.

As the method for subjecting the fibrous material to the treating liquid, a padding method, a dipping method, a spray method, a coating method, a print method and the like may be cited. Particularly, the padding method or the coating method is most advantageous in order to uniformly attach an inorganic type compound, a polyvinyl amine compound indicated by the general formula [I] or a hydrazide compound, and a synthetic resin, to the fibrous material with a high durability.

The padding method is a method in which a fibrous structural body or a resin formed article is dipped in a treating liquid containing an inorganic type compound, a polyvinyl amine compound indicated by the general formula [I] or a hydrazide compound, and a synthetic resin binder, for a suitable time, and then drawing or squeezing is performed using two rotational rolls. It is also possible to add to the treating liquid a texture processing agent, a finishing agent, for imparting softness, an antistatic agent, an antibacterial and anti-odor processing agent, a water repellency agent and the like, as long as the deodorizing characteristic is not particularly impaired.

The amount of synthetic resin binder to be attached is determined by the durability, texture and the like required for a deodorant formed article according to the present invention. If the binder is to be applied to a fibrous structural body by a padding method, it is applied normally in an amount of 0.01–10% owf and, preferably, 0.02–5% owf, in order to achieve soft texture and washing durability. If the amount applied is less than 0.01% owf, there is a tendency that the washing durability will become insufficient. If it greater than 10% owf, there is a tendency that the texture will become rough and hard.

If a coating method is used for applying the deodorant composition, the synthetic resin binder is used normally in the form of an emulsion or solution in an organic solvent. Although it is possible to mix an inorganic type compound, a polyvinyl amine compound indicated by the general formula [I] and/or a hydrazide compound, and a synthetic resin binder at substantially any desired ratio, it is preferred to add the inorganic type compound, the polyvinyl amine compound indicated by the general formula [I] and the hydrazide compound so that the total amount lies within the range of 0.05–50% by weight in terms of solid content. A treating liquid containing an inorganic type compound, a polyvinyl amine compound indicated by the general formula [I] or a hydrazide compound, and a synthetic resin binder, may contain additionally one or more compounds providing the desired viscosity and then used as a liquid to be applied for the coating. It is preferred to prepare the application liquid so that the viscosity is within the range of 500–50000 cps and, preferably, 1000–30000 cps, for improved film formability. The thickness of application is preferably 5–500 g/m$^2$·wet and, particularly preferably, 20–300 gm$^2$·wet.

As for the coating method, ordinary methods, for example, a knife coater, a roll coater, a slit coater and the like, may be used. A laminate method or a bonding method may also be used. After coating, the coating film is formed by a wet or dry method. It is also possible to perform chemical processing operations, such as a water repellency treatment, or physical processing operations, such as calendering and the like, after the formation of a coating film.

The heat treatment according to the present invention refers to dry heat treatment or wet heat treatment. The wet heat treatment includes immersion treatment and steam heat treatment. As the steam heat treatment, normal pressure saturated steam treatment, overheated steam treatment and high pressure steam treatment may be cited. The temperature of the dry heat treatment or the wet heat treatment should be within the range of about 80–210° C. If the heat treatment temperature is lower than 80° C., the washing durability becomes insufficient. If it exceeds 210° C., there is a danger that the fibrous material will become yellowed or brittle. For practical use, dry heat treatment at 110–190° C. is suitable.

The deodorant fibrous material of the present invention, obtained as described above, has a durable and excellent deodorizing characteristic for bad odors, such as ammonium, amines, hydrogen sulfide, mercaptans and the like, and aldehydes, acetic acid and the like contained in tobacco odors, and the like, and may still provide a soft texture.

The deodorant fibrous material of the present invention may suitably be used for building, bedding, interior or exterior materials that include curtains, carpets, mats, blankets, sheets, futon or comforter covers, pillowcases, futon or comforter wadding, automotive interior materials, and the like, and, moreover, can be used for a wide variety of applications, such as clothing materials for suits, uniforms, shirts, blouses, trousers, skirts, sweaters, socks, panty hoses, linings, interlinings and the like, materials for shoe sole inserts, shoe linings, bag shells, furoshiki or wrap-and-carry sheets, cushions, stuffed toy animals or the like, sanitary materials for cloth diapers, diaper covers and the like, deodorant materials for furniture, refrigerators and the like, filters and the like, non-woven fabrics, and the like.

Furthermore, the deodorant fibrous material wherein polyester fiber carrying a cycloalkane halide compound thereon is used as a fibrous material is particularly effective for building, bedding, interior or exterior materials requiring flame retardancy, such as curtains, carpets, mats, blankets, sheets, futon or comforter covers, pillowcases, futon or comforter wadding, automotive interior materials, and the like.

Examples will be described below. The washing method and the evaluation methods for flame retardancy and deodorizing characteristic employed for the examples are as follows.

[Washing Method]

Using, as a washing machine, an automatic reverse whirling type electric washing machine VH-3410 (by Toshiba (Kabushiki Gaisha)) and, as a detergent, 0.2% of "Zabu" (by Kao (Kabushiki Gaisha)), washing was performed in a strong reverse whirl mode at a temperature of 60±2° C. and a bath ratio of 1:40 for 75 minutes followed by a procedure of drainage and a 25- minute rinse with overflow, which procedure was repeated three times. This operation was determined as washing five times.

[Evaluation of Flame Retardancy]

Measurement was made by the JIS L 1091 D method (flame contact test).

[Evaluation of Deodorizing Characteristic by Detector Tube Method]

Ammonium gas was introduced into a 550-mL container containing a sample of 3 g so that the initial concentration became 200 ppm, and then the container was sealed. After the container was left for 30 minutes, the remaining ammonium concentration was measured by a detector gas tube.

Using odors of hydrogen sulfide, acetaldehyde and acetic acid, the initial concentrations were set to 20 ppm, 200 ppm and 20 ppm, respectively, and the remaining concentrations were measured, by similar methods.

[Olfactory Evaluation of Deodorizing Characteristic to Tobacco Odor]

After a cigarette producing smoke was placed, for 5 seconds, immediately under an inlet opening of a 500-mL glass-made Erlenmeyer flask held with the inlet opening facing down, the Erlenmeyer flask was quickly turned horizontally and, then, a sample of 3 g was introduced and the flask was sealed with a glass stopper. After the flask was left for one hour, the glass stopper was removed and the remaining odor was smelt for evaluation.

○: Substantially no odor remaining

Δ: Slight odor remaining

X : Considerable odor remaining

[Dispersibility of Inorganic Type Compound by Visual Observation]

The dispersibility of an inorganic type compound on fiber surfaces was checked by the finished surface quality.

○: Substantially no aggregation

Δ: Slight aggregation

X : Considerable aggregation

EXAMPLE 1

A polyester weave (#F1305GN by Toray (Kabushiki Gaisha), both warp and weft being 150 D-48 fil) that had been de-starched, after-treated and set by a dry heat treatment was used as a specimen fabric. After being dipped in a treating liquid having a composition indicated below, the specimen fabric was drawn or squeezed by a mangle (a draw or squeeze rate of 65%), dried at 120° C. for 3 minutes, and then dry heat- treated at 170° C. for 1 minute by a pin tenter.

With regard to the resultant fabric, the deodorizing characteristic and surface quality of the original fabric prior to washing and the state after being washed 10 times were evaluated. The results are shown in Tables 1 and 2.

An inorganic compound was used for treatment in the form of an emulsified-dispersed solution having a solid content of 45%. As the emulsifying-dispersing agent, the following non-ionic dispersion material was used.

Non-ionic dispersing agent:
   Isopropyl alcohol 3% owf
   Polyvinyl alcohol 1% owf
   Water 51% owf Composition of Treating Liquid
Inorganic compounds:
   Porous silicon dioxide fine particles 10 g/L
   Zinc sulfate 10 g/L
   Polyvinyl amine compound (a solid content of 45%) 10 g/L
   Synthetic resin: Elastoron W-11P (urethane based, a solid content of 25%) 20 g/L
   Catalyst: Elastoron Catalyst 64 0.5 g/L
   PH adjusting agent: Sodium hydrogen carbonate 0.05 g/L

EXAMPLE 2

A sample was produced by treating the same specimen fabric as in Example 1, except that the treating liquid had a composition indicated below.

With regard to the resultant fabric, the deodorizing characteristic and surface quality of the original fabric prior to washing and the state after being washed 10 times were evaluated. The results are shown in Tables 1 and 2.

Composition of Treating Liquid
Inorganic compounds:
   Porous titanium dioxide fine particles 10 g/L
   Copper sulfate 5 g/L
   Polyvinyl amine compound (a solid content of 45%) 10 g/L
   Synthetic resin: Elastoron W-11P (urethane based, a solid content of 25%) 20 g/L
   Catalyst: Elastoron Catalyst 64 0.5 g/L
   PH adjusting agent: Sodium hydrogen carbonate 0.05 g/L

EXAMPLE 3

A sample was produced by treating the same specimen fabric as in Example 1, except that the treating liquid had a composition indicated below.

With regard to the resultant fabric, the deodorizing characteristic and surface quality of the original fabric prior to washing and the state after being washed 10 times were evaluated. The results are shown in Tables 1 and 2.

Composition of Treating Liquid
Inorganic compounds:
   Porous titanium dioxide fine particles 10 g/L
   Copper sulfate 5 g/L
   Hydrazide: Hydrazide adipate 10 g/L
   Synthetic resin: Elastoron W-11P (urethane based, a solid content of 25%) 20 g/L
   Catalyst: Elastoron Catalyst 64 0.5 g/L
   PH adjusting agent: Sodium hydrogen carbonate 0.05 g/L

EXAMPLE 4

A sample was produced by treating the same specimen fabric as in Example 1, except that the treating liquid had a composition indicated below.

With regard to the resultant fabric, the deodorizing characteristic and surface quality of the original fabric prior to washing and the state after being washed 10 times were evaluated. The results are shown in Tables 1 and 2.

Composition of Treating Liquid

Inorganic compounds:

Porous fine particles formed of silicon dioxide and zinc oxide (silicon oxide: zinc oxide=3:1) 10 g/L Polyvinyl amine compound (a solid content of 45%) 10 g/L Synthetic resin: Elastoron W-11P (urethane based, a solid content of 25%) 20 g/L Catalyst: Elastoron Catalyst 64 0.5 g/L PH adjusting agent: Sodium hydrogen carbonate 0.05 g/L

EXAMPLE 5

A sample was produced by treating the same specimen fabric as in Example 1, except that the treating liquid had a composition indicated below.

With regard to the resultant fabric, the deodorizing characteristic and surface quality of the original fabric prior to washing and the state after being washed 10 times were evaluated. The results are shown in Tables 1 and 2.

Composition of Treating Liquid

Inorganic compounds:

Porous fine particles formed of silicon dioxide and zinc oxide (silicon oxide: zinc oxide=3:1) 10 g/L Polyvinyl amine compound (a solid content of 45%) 10 g/L Zinc polyacrylate 10 g/L Synthetic resin: Elastoron W-11P (urethane based, a solid content of 25%) 20 g/L Catalyst: Elastoron Catalyst 64 0.5 g/L PH adjusting agent: Sodium hydrogen carbonate 0.05 g/L

EXAMPLE 6

A sample was produced by applying a treating liquid having a composition described below to the same specimen fabric as used in Example 1 in an amount of 50 g/m$^2$·wet by a knife coating method, and then performing a dry heat treatment at 120° C. for 5 minutes.

With regard to the resultant fabric, the deodorizing characteristic and surface quality of the original fabric prior to washing and the state after being washed 10 times were evaluated. The results are shown in Tables 1 and 2.

Inorganic compounds:

Porous titanium dioxide fine particles 10 parts

Copper sulfate 1 part

Hydrazide compound: Hydrazide malate 1 part

Synthetic resin: Acryl based resin (a solid content of 45%) 50 parts

Non-ionic type viscosity bodying agent 5 part

Water 33 parts

EXAMPLE 7

The same specimen fabric as used in Example 1 was treated in a bath comprising 3.0% owf of a disperse dye Dianix Black BC-FS 200% (by Deister Japan (Kabushiki Gaisha)), 0.5 cc/L of acetic acid (80%), 0.5 g/L of a dispersing agent RAP-50 (by Sanyo Kasei Kogyo (Kabushiki Gaisha)), and 15% owf of 1,2,5,6,9,10-sexabromocyclododecane (HBCD), at 130° C. for 45 minutes, and then reduced and washed by an ordinary method and then washed with hot water and dried.

After being dipped in a treating liquid having a composition indicated below, the specimen fabric was drawn or squeezed by a mangle (a draw or squeeze rate of 65%), dried at 120° C. for 3 minutes, and then dry heat-treated at 170° C. for 1 minute by a pin tenter, thereby producing a sample.

With regard to the resultant fabric, the deodorizing characteristic and surface quality of the original fabric prior to washing and the state after being washed 10 times were evaluated. The results are shown in Tables 1 and 2.

Composition of Treating Liquid

Inorganic compounds:

Porous fine particles formed of silicon dioxide and zinc oxide (silicon oxide: zinc oxide=3:1) 10 g/L Copper sulfate 5 g/L Polyvinyl amine compound (a solid content of 45%) 10 g/L Synthetic resin: Elastoron W-11P (urethane based, a solid content of 25%) 5 g/L Catalyst: Elastoron Catalyst 64 0.1 g/L PH adjusting agent: Sodium hydrogen carbonate 0.02 g/L

EXAMPLE 8

The same specimen fabric as used in Example 1 was treated in a bath comprising 3.0% owf of a disperse dye Dianix Black BG-FS 200% (by Deister Japan (Kabushiki Gaisha)), 0.5 cc/L of acetic acid (80%), 0.5 g/L of a dispersing agent RAP-50 (by Sanyo Kasei Kogyo (Kabushiki Gaisha)), and 15% owf of 1,2,5,6,9,10-sexabromocyclododecane (HBCD), at 130° C. for 45 minutes, and then reduced and washed by an ordinary method and then washed with hot water and dried.

After being dipped in a treating liquid having a composition indicated below, the specimen fabric was drawn or squeezed by a mangle (a draw or squeeze rate of 65%), dried at 120° C. for 3 minutes, and then dry heat-treated at 170° C. for 1 minute by a pin tenter, thereby producing a sample.

With regard to the resultant fabric, the deodorizing characteristic and surface quality of the original fabric prior to washing and the state after being washed 10 times were evaluated. The results are shown in Tables 1 and 2.

Composition of Treating Liquid

Block copolymer: TO-SR-1 (a solid content of 10%) 20 g/L

Inorganic compounds:

Porous silicon dioxide fine particles 10 g/L

Zinc sulfate 10 g/L

Polyvinyl amine compound (a solid content of 45%) 10 g/L

Synthetic resin: Elastoron W-11P (urethane based, a solid content of 25%) 20 g/L Catalyst: Elastoron Catalyst 64 0.5 g/L PH adjusting agent: Sodium hydrogen carbonate 0.05 g/L

COMPARATIVE EXAMPLE 1

A sample was produced by treating the same specimen fabric as in Example 1, except that the treating liquid had a composition indicated below.

With regard to the resultant fabric, the deodorizing characteristic and surface quality of the original fabric prior to washing and the state after being washed 10 times were evaluated. The results are shown in Tables 1 and 2.

Composition of Treating Liquid
Inorganic compounds:
  Porous silicon dioxide fine particles 10 g/L
  Zinc sulfate 10 g/L
Synthetic resin: Elastoron W-11P (urethane based, a solid content of 25%) 20 g/L
Catalyst: Elastoron Catalyst 64 0.5 g/L
PH adjusting agent: Sodium hydrogen carbonate 0.05 g/L

COMPARATIVE EXAMPLE 2

A sample was produced by treating the same specimen fabric as in Example 1, except that the treating liquid had a composition indicated below.

With regard to the resultant fabric, the deodorizing characteristic and surface quality of the original fabric prior to washing and the state after being washed 10 times were evaluated. The results are shown in Tables 1 and 2.

Composition of Treating Liquid

Polyvinyl amine compound (a solid content of 45%) 10 g/L
Synthetic resin: Elastoron W-11P (urethane based, a solid content of 25%) 20 g/L
Catalyst: Elastoron Catalyst 64 0.5 g/L
PH adjusting agent: Sodium hydrogen carbonate 0.05 g/L

COMPARATIVE EXAMPLE 3

A sample was produced by treating the same specimen fabric as in Example 1, except that the treating liquid had a composition indicated below.

With regard to the resultant fabric, the deodorizing characteristic and surface quality of the original fabric prior to washing and the state after being washed 10 times were evaluated. The results are shown in Tables 1 and 2.

Composition of Treating Liquid
Inorganic compounds:
  Porous silicon dioxide fine particles 10 g/L
  Zinc sulfate 10 g/L
  Polyvinyl amine compound (a solid content of 45%) 10 g/L

COMPARATIVE EXAMPLE 4

A sample was produced by treating the same specimen fabric as in Example 1, except that an emulsifying-dispersing agent for an inorganic compound was not used, and that the treating liquid had a composition indicated below. In the resultant fabric, the porous silicon dioxide fine particles were very poorly dispersed, and the cloth was blotched. Nonetheless, the evaluation was normally performed. The deodorizing characteristic and surface quality of the original fabric prior to washing and the state after being washed 10 times were evaluated. The results are shown in Tables 1 and 2.

Composition of Treating Liquid
Inorganic compounds:
  Porous silicon dioxide fine particles 10 g/L
  Zinc sulfate 10 g/L
  Polyvinyl amine compound (a solid content of 45%) 10 g/L From Tables 1 and 2, it can been seen that the fabrics in Examples 1–7 had excellent deodorizing characteristics after being washed ten times, as well as before the washing. It can also be seen that Examples 6–7, which were treated for flame retardancy, maintained excellent flame retardancy even after being washed ten times.

INDUSTRIAL APPLICABILITY

The present invention can be applied to clothing, household articles, interior products, various industrial materials, and the like, that have high-level deodorizing function.

TABLE 1

| | Ammonium | | Hydrogen sulfide | | Acetaldehyde | | Acetic acid | |
|---|---|---|---|---|---|---|---|---|
| | Original fabric | After washing | Original fabric | After washing | Original fabric | After washing | Original fabric | After washing |
| Example 1 | ND | 8 | ND | ND | ND | 30 | 1 | 2 |
| Example 2 | ND | 5 | ND | ND | ND | 20 | ND | 1 |
| Example 3 | ND | 6 | ND | ND | 5 | 40 | 1 | 3 |
| Example 4 | ND | 3 | ND | ND | ND | 20 | ND | 2 |
| Example 5 | ND | ND | ND | ND | 4 | 40 | ND | 1 |
| Example 6 | ND | 3 | ND | ND | 4 | 40 | ND | 1 |
| Example 7 | ND | 10 | ND | 1 | ND | 40 | ND | 4 |
| Example 8 | ND | 12 | ND | ND | ND | 40 | 1 | 3 |
| Comparative Example 1 | ND | 10 | ND | ND | 170 | 180 | 2 | 3 |
| Comparative Example 2 | 150 | 180 | 17 | 18 | ND | 20 | 17 | 19 |
| Comparative Example 3 | ND | 170 | ND | 18 | ND | 150 | 1 | 18 |
| Comparative Example 4 | ND | 170 | ND | 20 | ND | 170 | 1 | 19 |

After washing: After washing ten times.
ND: No detected.

TABLE 2

| | Difactory evaluation with tobacco odor | | Flame retardancy Number of flame contacts | | Surface quality |
|---|---|---|---|---|---|
| | Original fabric | After washing | Original fabric | After washing | Original fabric |
| Example 1 | o | o | — | — | o |
| Example 1 | o | o | — | — | o |
| Example 1 | o | o | — | — | o |
| Example 1 | o | o | — | — | o |
| Example 1 | o | o | — | — | o |
| Example 1 | o | o | — | — | o |
| Example 1 | o | o | 5.0 | 5.5 | o |
| Example 1 | o | o | 5.0 | 6.0 | o |
| Comparative Example 4 | x | x | — | — | o |
| Comparative Example 4 | x | x | — | — | o |
| Comparative Example 4 | o | x | — | — | o |
| Comparative Example 4 | o | x | — | — | x |

After washing: After washing ten times

What is claimed is:

1. A deodorant fibrous material comprising a fibrous material having a surface to which is attached a deodorant composition comprising:
    (1) a first deodorant material selected from at least one of an inorganic component, a polyorganic acid component, a polyorganic acid salt component and a polyorganic acid ester component said inorganic component providing at least one inorganic element;
    (2) a second deodorant material comprising a polyvinyl amine compound of the formula:

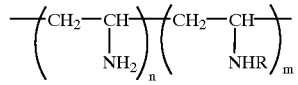

wherein R is a group selected from CHO, and $CH_3CO$ groups, n is an integer between about 150–4,650, m is an integer between about 0–150; and
    (3) a synthetic resin binder.

2. The deodorant fibrous material according to claim 1, wherein said first deodorant material is an inorganic component comprising a porous substance and at least one compound selected from the group consisting of metallic compounds of cooper, zinc, silver, lead, iron, aluminum, calcium, magnesium, manganese, nickel and cobalt.

3. The deodorant fibrous material according to claim 2, wherein said inorganic component comprises a porous substance and a copper compound.

4. The deodorant fibrous material according to claim 2, where said inorganic component comprises a porous substance and a zinc compound.

5. The deodorant fibrous material according to claim 2, wherein said porous substance is at least one selected from the group consisting of silicon dioxide, titanium dioxide, zinc oxide, aluminum oxide, zeolite, silica gel and active carbon.

6. The deodorant fibrous material according to claim 1, wherein said first deodorant material is uniformly dispersed on the surface of the fibrous material.

7. The deodorant fibrous material according to claim 1, wherein said deodorant composition further comprises, as an emulsifying dispersing agent for the said first deodorant material, a polyvinyl alcohol having a molecular weight of about 2,000–100,000 and a solvent to penetrate the fibrous material.

8. The deodorant fibrous material according to claim 1, wherein said synthetic resin binder is at least one resin selected from the group consisting of urethane resins, acrylic resins, aminoplast resins, epoxy resins, glyoxal resins and ethylene urea resins.

9. The deodorant fibrous material according to claim 1, wherein at least a proportion of said first deodorant material is selected from at least one of poly-organic acids, poly-organic acid esters and poly-organic acid salts.

10. The deodorant fibrous material according to claim 9, wherein said first deodorant material additionally comprises, as an inorganic component, a porous substance.

11. The deodorant fibrous material according to claim 1, wherein said fibrous material is a polyester fiber.

12. The deodorant fibrous material according to claim 11, wherein said polyester fiber contains a cycloalkane halide compound as a flame retardant.

13. The deodorant fibrous material according to claim 1, wherein said deodorant composition further comprises, as a flame retardant agent, a copolymer of a polyalkylene glycol with an aromatic dicarboxylic acid and an alkylene glycol.

14. A deodorant fibrous product formed from a deodorant fibrous material comprising a fibrous material having a surface to which is attached a deodorant composition comprising:
    (1) a first deodorant material selected from at least one of an inorganic component, a polyorganic acid component, a polyorganic acid salt component and a polyorganic acid ester component;
    (2) a second deodorant material comprising a polyvinyl amine compound of the formula:

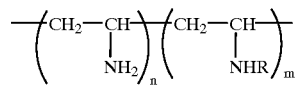

wherein R is a group selected from CHO, and $CH_3CO$ groups, n is an integer between about 150–4,650, m is an integer between about 0–150; and
    (3) a synthetic resin binder.

15. A method of producing a deodorant fibrous material, which method comprises applying to a surface of a fibrous material a liquid deodorant composition comprising:

(1) a first deodorant material selected from at least one of an inorganic component, a polyorganic acid component, a polyorganic acid salt component a and polyorganic acid ester components said inorganic component providing at least one inorganic element;

(2) a second deodorant material comprising a polyvinyl amine compound of the formula:

wherein R is a group selected from CHO, and $CH_3CO$ groups, n is an integer between about 150–4,650, m is an integer between about 0–150; and (3) a synthetic resin binder, and thereafter subjecting the fibrous material to heat treatment.

16. The method according to claim 15, wherein said liquid deodorant composition is applied by a method selected from padding and coating.

17. The method according to claim 15, further comprising the step of immersing said fibrous material in a treatment bath of a liquid containing a cycloalkane halide compound prior to the application of said liquid deodorant composition.

* * * * *

UNITED STATES PATENT AND TRADEMARK OFFICE
CERTIFICATE OF CORRECTION

PATENT NO.   : 6,077,794
DATED        : June 20, 2000
INVENTOR(S)  : Jirou Tabata; Toshiharu Kanaya; Masayuki Hirata; Kouichi Saito; Kouji Hori; Kouichi Kawaguchi It is certified that error appears in the above-identified patent and that said Letters Patent is hereby corrected as shown below:

Column 2,
Line 8, please change "CH3" to -- $CH_3$ --.

Column 6,
Line 28, please change "—(Cn Hc 2n O)—(n=2-4)" to -- —$(C_nH_{2n}O)$— (n=2-4) --.

Column 8,
Line 14, please change "gm$^2$" to -- $g/m^2$ --.

Column 15, table 2,
Line 2, (after the first "Example 1") please change "Example 1" to -- Example 2 --;
Line 3, please change "Example 1" to -- Example 3 --;
Line 4, please change "Example 1" to -- Example 4 --;
Line 5, please change "Example 1" to -- Example 5 --;
Line 6, please change "Example 1" to -- Example 6 --;
Line 7, please change "Example 1" to -- Example 7 --;
Line 8, please change "Example 1" to -- Example 8 --;
Line 10, please change "Example 4" to -- Example 1 --;
Line 12, please change "Example 4" to -- Example 2 --; and
Line 14, please change "Example 4" to -- Example 3 --.

Column 17,
Line 6, after "component", second occurrence, please delete "a"; and
Line 7, after "components", please insert ",".

Signed and Sealed this

Eleventh Day of September, 2001

Attest:

NICHOLAS P. GODICI
Attesting Officer    Acting Director of the United States Patent and Trademark Office